United States Patent
Iafisco et al.

(10) Patent No.: US 11,377,353 B2
(45) Date of Patent: Jul. 5, 2022

(54) STABILIZED AMORPHOUS CALCIUM PHOSPHATE DOPED WITH FLUORIDE IONS AND A PROCESS FOR PRODUCING THE SAME

(71) Applicant: CURASEPT A.D.S. S.R.L., Saronno (IT)

(72) Inventors: Michele Iafisco, Castel Maggiore (IT); Anna Tampieri, Faenza (IT)

(73) Assignee: CURASEPT A.D.S. S.R.L., Saronno (IT)

( * ) Notice: Subject to any disclaimer, the term of this patent is extended or adjusted under 35 U.S.C. 154(b) by 0 days.

(21) Appl. No.: 17/255,522

(22) PCT Filed: Jun. 27, 2019

(86) PCT No.: PCT/EP2019/067188
§ 371 (c)(1),
(2) Date: Dec. 23, 2020

(87) PCT Pub. No.: WO2020/002517
PCT Pub. Date: Jan. 2, 2020

(65) Prior Publication Data
US 2021/0276869 A1    Sep. 9, 2021

(30) Foreign Application Priority Data
Jun. 28, 2018   (IT) .................. 102018000006753

(51) Int. Cl.
*C01B 25/32*      (2006.01)
*A61K 6/54*       (2020.01)
(Continued)

(52) U.S. Cl.
CPC .............. *C01B 25/327* (2013.01); *A61K 6/17* (2020.01); *A61K 6/54* (2020.01); *A61K 6/864* (2020.01);
(Continued)

(58) Field of Classification Search
CPC .......... C01B 25/327; A61K 6/17; A61K 6/54; A61K 6/864; C01P 2004/04;
(Continued)

(56) References Cited

U.S. PATENT DOCUMENTS
2006/0110306 A1    5/2006   Chow et al.

FOREIGN PATENT DOCUMENTS
| | | |
|---|---|---|
| CN | 103876945 A | 6/2014 |
| WO | 2016012452 A1 | 1/2016 |
| WO | 2017025359 A1 | 2/2017 |

OTHER PUBLICATIONS

Chatzipanagis, et al., Crystallization of citrate-stabilized amorphous calcium phosphate to nanocrystaline apatite: a surface-mediated transformation, ChrystEngComm 2016; 18: 3170-3173, with Electronic Supplementary Information (Year: 2016).*

(Continued)

*Primary Examiner* — Daniel C. McCracken
(74) *Attorney, Agent, or Firm* — Abelman, Frayne & Schwab

(57) ABSTRACT

The invention relates to a process for the preparation of a citrate-coated amorphous calcium phosphate nanoparticle which comprises the following steps: 1) providing a first solution of a salt of calcium and a citrate salt wherein the molar ratio of citrate ion to calcium ion is in the range from 1 to 2 thus obtaining a clear first solution; 2) providing a second solution of a salt capable to give phosphate anion and a carbonate salt; 3) mixing together the first and the second solution at a pH in the range from 8 to 11; 4) precipitating the nanoparticle; and 5) drying the nanoparticle obtained from step 4). Preferably and advantageously the invention provides for the addition of a fluoride compound in step 2) for obtaining a fluorine-doped citrate-coated calcium phosphate nanoparticle or a nanoparticle agglomerate. The nanoparticle/nanoparticle agglomerate of the invention has a (Continued)

peculiar superficial area and a diameter that allow to use it as a biomaterial for dentistry application.

27 Claims, 10 Drawing Sheets

(51) Int. Cl.
  *A61K 6/864*   (2020.01)
  *A61K 6/17*   (2020.01)
  *B82Y 5/00*   (2011.01)
  *B82Y 30/00*   (2011.01)
  *B82Y 40/00*   (2011.01)

(52) U.S. Cl.
  CPC ............... *B82Y 5/00* (2013.01); *B82Y 30/00* (2013.01); *B82Y 40/00* (2013.01); *C01P 2002/01* (2013.01); *C01P 2002/02* (2013.01); *C01P 2004/03* (2013.01); *C01P 2004/04* (2013.01); *C01P 2004/50* (2013.01); *C01P 2004/64* (2013.01); *C01P 2006/12* (2013.01)

(58) Field of Classification Search
  CPC .............. C01P 2004/03; C01P 2006/12; C01P 2004/64; C01P 2004/50; C01P 2002/02; C01P 2002/01; B82Y 30/00; B82Y 5/00; B82Y 40/00
  See application file for complete search history.

(56) References Cited

OTHER PUBLICATIONS

International Search Report from corresponding PCT Application No. PCT/EP2019/067188 dated Oct. 24, 2019.

* cited by examiner

STABILIZED AMORPHOUS CALCIUM PHOSPHATE DOPED WITH FLUORIDE IONS AND A PROCESS FOR PRODUCING THE SAME

CROSS REFERENCE TO RELATED APPLICATION

This application claims benefit under 35 U.S.C. § 371 to international application No. PCT/EP2019/067188 filed on Jun. 27, 2019, which claims priority to Italian application No. 102018000006753 filed Jun. 28, 2018, the contents of which are incorporated by reference in their entireties.

FIELD OF THE INVENTION

The present invention concerns biomaterials to be used in medicine, preferably in dentistry. Specifically, the invention relates to particles of citrate-coated amorphous calcium phosphate, preferably doped with fluoride ions and a process for producing the same. The invention also relates to the use of the particle of the invention as a biomaterial in medicine, preferably in dentistry as biomaterial for tooth remineralization and dentin desensitizer.

PRIOR ART

Amorphous calcium phosphate (ACP) is one of the most important calcium phosphate (CaP) phase in biomineralization science as well as in the biomedical materials field. ACP occurs in many biological systems, especially in primitive organisms, mainly as reservoir of $Ca^{2+}$ and $PO_4^{3-}$ ions. ACP is the first phase precipitated from a supersaturated aqueous solution containing $Ca^{2+}$ and $PO_4^{3-}$ ions due to its lower surface energy than that of hydroxyapatite (HA) and octacalcium phosphate (OCP). ACP is a mineral phase with a short-range order, rather than crystalline long-range order. The basic structural unit of ACP, as proposed by Betts and Posner, is a roughly spherical cluster of ions having an average diameter of 9.5 nm consistent with the chemical composition $Ca_9(PO_4)_6$. It is known that ACP is an unstable material and it transforms into more thermodynamically stable CaP phases (i.e. HA and OCP) in solution as well as in dry state, reacting with water in the atmosphere thus evidently exacerbating the problem of the stability of ACP when used as final biomaterial.

ACP is currently studied to manufacture several biomaterials thanks to its excellent bioactivity, high cell adhesion, tailorable biodegradation and good osteoconductivity. It is used, for example, in the preparation of coatings on metallic prostheses, self-settings injectable cements and hybrid composites with polymers.

ACP is a particularly appealing material in dentistry as enamel remineralizing agents due to their ability to release significant amount of $Ca^{2+}$ and $PO_4^{3-}$ ions, as compared with other crystalline CaP phase. These agents can be added to restorative materials or directly applied on tooth surface to penetrate into the enamel subsurface lesions. ACP has been proposed to be an essential precursor phase during the formation of mineralized tissue. Therefore, the use of ACP can provide a biomimetic remineralization strategy by mimicking the biomineralization processes that form new mineral phase.

Demineralization of dental hard tissues (enamel and dentin) is the main responsible for dental caries and dentin hypersensitivity. It is caused by a low pH environment which, in turn, has three main causes: intake of acidic food or drinks, the presence of gastroesophageal reflux disease or the acidogenic activity of a pathogenic oral biofilm. When the pH value of the saliva drops below 5.5, hydroxyapatite (HA), which is the main mineral constituent of the dental tissues representing in enamel and dentine the 95 wt % and 75 wt %, respectively, starts to dissolve.

Demineralization is a reversible process if the damaged tissue is exposed to oral environment that favors rem ineralization. For example, the enamel cavities caused by demineralization processes are naturally remineralized by the epitaxial growth of residual crystals acting as nucleation sites, with the saliva providing a supersaturated $Ca^{2+}$ and $PO_4^{3-}$ ions environment respect to HA. However, remineralization of enamel by saliva is seldom completely achieved, especially when there is an imbalance in duration and extent of demineralization/remineralization phases. To efficiently reverse demineralization and boost remineralization, the use of an external source supplying $Ca^{2+}$ and $PO_4^{3-}$ ions possibly in the crystal lesions and voids to increase the supersaturation of HA and produce a net mineral gain can be helpful. Therefore several formulations containing different forms of CaP (i.e. HA, fluoro-hydroxyapatite (FHA), tetracalcium phosphate (TTCP), beta-tricalcium phosphate (β-TCP), ACP, etc.) have been reported as healing agents for enamel demineralization. However, the main problem with applying a crystalline CaP phase in the oral cavity to promote remineralization is its poor solubility, particularly in the presence of fluoride ions, such that the $Ca^{2+}$ and $PO_4^{3-}$ ions are unavailable.

It was recently reported that citrate plays a key dual role in the HA crystallization: driving a growth pathway via an amorphous precursor and controlling the size of nanoparticles by the non-classical oriented aggregation crystal growth mechanism. Furthermore, fluoride is the most widely employed prophylactic agent to reduce and prevent enamel demineralization, remaining so far as the most effective agent for caries prevention. Fluoride is thought to work by two different mechanisms: i) replacing of the hydroxyl groups of the new formed HA, resulting in fluorapatite [FHA, $Ca_5(PO_4)_3F$], which is less soluble and thus more resistant to acid attack than HA; ii) inhibiting the metabolic and physiological pathways of microorganisms in the cariogenic biofilm that produce organic acids to demineralize dental tissue. A first object of the present invention is hence the delivery of $Ca^{2+}$, $PO_4^{3-}$ and $F^-$ in the enamel lesions leading to an improved remineralizing effect, and at the same time the occlusion of the dentinal tubules.

In WO2016/012452A1 it is described a process for obtaining fluoride-doped citrate-coated amorphous calcium phosphate nanoparticles, that can be applied in medicine and in products for dentistry such as mouthwashes, toothpastes, chewing gums as a remineralizing agent of enamel and dentine.

Specifically, the process herein described comprises the following steps:
- the preparation of a $CaCl_2$) solution at a concentration comprised between 0.08 M and 0.12 M and sodium citrate at a concentration comprised between 0.35 M and 0.50 M;
- the preparation of a second solution formed by $Na_2HPO_4$ at a concentration comprised between 0.10 M and 0.15 M with $Na_2CO_3$ 0.2 M and a fluoride compound;
- mixture under stirring of the two solutions prepared in the previous stages in the proportion 1:1 v/v at a pH comprised between 8.3 and 8.7 (adjusted, for example, with HCl) and at room temperature for a time period of less than 2 minutes;

three successive sedimentation cycles by centrifugation, removal of the supernatant and washing of the precipitate with ultrapure water; and freeze-drying of the wet precipitate.

This process allows to obtain nanoparticles that resulted to have a biological response in osteoblast cells, specifically a cell proliferation was observed at different nanoparticle concentrations, while being completely biocompatible in contact with the osteoblast cell.

Even if the nanoparticles of WO2016/012452 resulted to be a good biomaterial adapted for the remineralization of the enamel, there is still the need to have biomaterials that are effective and capable to act as a remineralizing agent in a brief period of time.

SUMMARY OF THE INVENTION

The inventors of the present invention have surprisingly found a process for the preparation of a citrate-coated amorphous calcium phosphate nanoparticle which comprises the following steps:
1) providing a first solution of a salt of calcium and a citrate salt wherein the molar ratio of citrate ion to calcium ion is in the range from 1 to 2 thus obtaining a clear first solution;
2) providing a second solution of a salt capable to give phosphate anion and a carbonate salt;
3) mixing together the clear first solution and the second solution at a pH in the range from 8 to 11;
4) precipitating the nanoparticle; and
5) drying the nanoparticle obtained from step 4).

In the process of the invention the first solution is clear before the mixing step is carried out. The expression "clear first solution" means that the first solution is substantially free of any kind of particulate.

Advantageously step 5) is a freeze-drying step.

In another aspect the invention concerns a citrate-coated amorphous calcium phosphate nanoparticle obtainable by the process according to the invention, wherein the drying step 5) is a freeze-drying step, being said nanoparticle characterized by a superficial area from $250\ m^2\ g^{-1}$ to $360\ m^2\ g^{-1}$ as measured with Brunauer-Emmett-Teller (BET) gas adsorption method and having a round-shaped morphology with diameter in the range from 30 to 80 nm as measured by transmission electron microscopy (TEM) images.

In a first embodiment hence, the superficial area of the nanoparticle is in the range from $250\ m^2\ g^{-1}$ to $360\ m^2\ g^{-1}$ as measured with Brunauer-Emmett-Teller (BET) gas adsorption method by using powdered samples and a Sorpty 1750 (Carlo Erba, Milan Italy) and said nanoparticle has preferably a round-shaped morphology with a diameter in the range from 30 to 80 nm. All the instruments used for determining the diameter are instruments capable to have transmission electron microscopy (TEM) images.

Advantageously step 5) is a spray-drying step.

In another aspect the invention concerns a citrate-coated amorphous calcium phosphate nanoparticle agglomerate obtainable by the process according to the invention, wherein the drying step 5) is a spray-drying step, being said nanoparticle agglomerate characterized by a superficial area from $3\ m^2\ g^{-1}$ to $10\ m^2\ g^{-1}$ as measured with Brunauer-Emmett-Teller (BET) gas adsorption method and having a spherical shape with diameter in the range from 2 to 25 μm as measured by scanning electron microscopy (SEM).

As it will be evident also by the below experimental part when step 5) consists in a spray drying step, the final product is an agglomerate of nanoparticles corresponding to a microparticle having a diameter in the range from 2 to 25 μm. In a second embodiment hence, the superficial area of the nanoparticle agglomerate is in the range from $3\ m^2\ g^{-1}$ to $10\ m^2\ g^{-1}$ as measured with Brunauer-Emmett-Teller (BET) gas adsorption method by using powdered samples and a Sorpty 1750 (Carlo Erba, Milan Italy) and said nanoparticle agglomerate has preferably a spherical shape and a diameter in the range from 2 to 25 μm. All the instruments used for determining the diameter are instruments for scanning electron microscopy (SEM).

In a further and preferred aspect of the invention allows to obtain a fluorine-doped citrate-coated amorphous calcium phosphate nanoparticle by providing of adding a fluoride compound in the second solution of step 2).

Therefore in another and preferred aspect the invention concerns a fluorine-doped citrate-coated amorphous calcium phosphate nanoparticle obtainable by the process according to the invention and comprising the addition of a fluoride compound in step 2), wherein the drying step 5) is a freeze-drying step, being said nanoparticle characterized by a superficial area from $250\ m^2\ g^{-1}$ to $370\ m^2\ g^{-1}$ as measured with Brunauer-Emmett-Teller (BET) gas adsorption method and having round-shaped morphology with diameter in the range from 30 to 80 nm as measured by transmission electron microscopy (TEM) images.

In a first embodiment hence, the superficial area of fluorine-doped citrate-coated amorphous calcium phosphate nanoparticle is in the range from $250\ m^2\ g^{-1}$ to $370\ m^2\ g^{-1}$ as measured with Brunauer-Emmett-Teller (BET) gas adsorption method by using powdered samples and a Sorpty 1750 (Carlo Erba, Milan Italy) and said nanoparticle has preferably a round-shape with a diameter in the range from 30 to 80 nm. All the instruments used for determining the diameter are instruments capable to have transmission electron microscopy (TEM) images.

In another and preferred aspect the invention concerns a fluorine-doped citrate-coated amorphous calcium phosphate nanoparticle agglomerate obtainable by the process according to the invention and comprising the addition of a fluoride compound in step 2), wherein the drying step 5) is a spray-drying step, being said nanoparticle agglomerate characterized by a superficial area from $3\ m^2\ g^{-1}$ to $10\ m^2\ g^{-1}$ as measured with Brunauer-Emmett-Teller (BET) gas adsorption method and having a diameter in the range from 2 to 25 μm as measured by scanning electron microscopy (SEM).

The superficial area is measured with Brunauer-Emmett-Teller (BET) gas adsorption method by using powdered samples and a Sorpty 1750 (Carlo Erba, Milan Italy).

In a further aspect the invention concerns the use of the nanoparticle or the nanoparticle agglomerate of the invention as a biomaterial in the treatment of the oral cavity, generally in dentistry. Preferably the biomaterial is used as a remineralization agent, preferably for the dental hard tissues remineralization, or as dentin desensitizer, where in this latter case its action is preferably to fill and occlude the dentinal tubules.

Specifically, the biomaterial is a remineralization agent, preferably in case of abfraction, erosion, cavity, abrasion, white spot and hypomineralization.

In a still further aspect the invention concerns the use of a particle of the invention as a biomaterial in orthopaedic applications.

Surprisingly the citrate-stabilized nanoparticle and the fluorine-doped citrate-stabilized nanoparticle of the invention have a high superficial area that resulted to be capable to deliver $Ca^{2+}$ and $F^{1-}$ ions in a very fast way, certainly faster than the nanoparticles of the prior art such as those described in WO2016/012452.

Without being bound to any specific theory and as it will be more explained in the experimental part, the inventors deem that the surprising property of delivering in very fast way the $Ca^{2+}$ and $F^{1-}$ ions is due to the process, i.e. the molar ratio of citrate ion to calcium ion in the range from 1 to 2.

DETAILED DESCRIPTION OF THE INVENTION

Figure 1A:
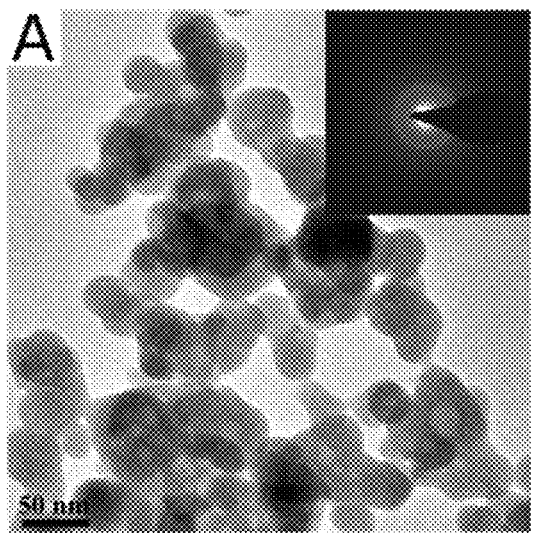
FIG. 1A shows TEM micrograph of $ACP^4$ prepared in example 1; (inset: corresponding SAED pattern)

Therefore the invention relates to a process for the preparation of a citrate-coated amorphous calcium phosphate nanoparticle, which comprises the following steps:

1) providing a first solution of a salt of calcium and a citrate salt wherein the molar ratio of citrate ion to calcium ion is in the range from 1 to 2 thus obtaining a clear first solution;

2) providing a second solution of a salt capable to give phosphate anion and a carbonate salt;

3) mixing together the clear first solution and the second solution at a pH in the range from 8 to 11;

4) precipitating the nanoparticle; and 5) drying the nanoparticle obtained from step 4).

The step 1) of the process consists in providing a first solution of a salt of calcium and of a citrate salt, wherein the molar ratio of citrate ion to calcium ion is in the range from 1 to 2. The first solution so obtained is clear.

The salt of calcium is preferably made of an anion selected from the group consisting of chloride, nitrate, hydroxide, acetate, oxalate, lactate, more preferably the anion is chloride.

The salt of citrate is preferably made of a cation selected from the group consisting of sodium and potassium, more preferably the cation is sodium.

More preferably the molar ratio of citrate ion to calcium ion is about 1.

Still more preferably, the molar ratio of citrate ion to calcium ion is about 2. In a preferred embodiment, the first solution of step 1) of the process according to the invention comprises at least one further salt selected from the group of: strontium salt, and magnesium salt.

The strontium salt is preferably made of an anion selected from the group consisting of chloride, nitrate, hydroxide, acetate, oxalate, lactate, more preferably the anion is chloride.

The magnesium salt is preferably made of an anion selected from the group consisting of chloride, nitrate, hydroxide, acetate, oxalate, lactate, more preferably the anion is chloride.

Step 2) consists in providing a second solution of a salt capable to give phosphate anion and a carbonate salt.

Preferably the ratio between the carbonate anion and phosphate is in the range from 1 to 1.66.

Preferably the salt capable to give phosphate anion is a salt of phosphate, hydrogen phosphate or hydrogen phosphate. The salt capable to give phosphate anion is preferably made of a cation select from the group consisting of sodium, potassium and ammonium, more preferably the cation is sodium.

Step 3) consists in mixing together the first and the second solution at a pH in the range from 8 to 11, preferably 8.5-10.7.

In an advantageous aspect the ratio of the first and the second solution is in the range 1:1 to 1:1.5.

According to the invention the mixing step 3) is carried out after the first solution is clear. Preferably the second solution is added to the clear first solution for the mixing step.

The step 4) consists in precipitating the nanoparticle.

The step of precipitation can advantageously be carried out by providing sedimentation cycles by centrifugation, after which the removal of supernatant can be carried out according to well-known methods. As soon as the precipitate is collected, it can be washed with preferably ultrapure water. The wet precipitate is then dried according to drying methods known in the art.

Step 5) consists in a drying step of the precipitated nanoparticle of the invention. The drying step can be carried out with any suitable means known in the art. Preferably the drying step can be selected from freeze-drying, spray-drying and ventilated oven drying. This latter is preferably carried out after washing with ethanol and at a temperature of about 40° C.

In a preferred aspect the drying step 5) is a freeze-drying step.

In another aspect the invention concerns a citrate-coated amorphous calcium phosphate nanoparticle obtainable by the process according to the invention, wherein the drying step 5) is a freeze-drying step, being said nanoparticle characterized by a superficial area from 250 m² g⁻¹ to 360 m² g⁻¹, preferably from 270 m² g⁻¹ to 360 m² g⁻¹, as measured with Brunauer-Emmett-Teller (BET) gas adsorption method and having a round-shaped morphology with a diameter in the range from 30 to 80 nm as measured by transmission electron microscopy (TEM) images.

In a first embodiment hence, the superficial area of the nanoparticle is in the range from 250 m² g⁻¹ to 360 m² g⁻¹, preferably from 270 m² g⁻¹ to 360 m² g⁻¹, as measured with Brunauer-Emmett-Teller (BET) gas adsorption method by using powdered samples and a Sorpty 1750 (Carlo Erba, Milan Italy) and said nanoparticle has preferably a spherical shape with a diameter in the range from 30 to 80 nm. All the instruments used for determining the diameter are instruments capable to have transmission electron microscopy (TEM) images.

In a further advantageous aspect the drying step 5) is a spray-drying step.

In another aspect the invention concerns a citrate-coated amorphous calcium phosphate nanoparticle agglomerate obtainable by the process according to the invention, wherein the drying step 5) is a spray-drying step, being said nanoparticle agglomerate characterized by a superficial area from 3 m² g⁻¹ to 10 m² g⁻¹ as measured with Brunauer-Emmett-Teller (BET) gas adsorption method and having a round-shaped morphology with a diameter in the range from 2 to 25 μm as measured by scanning electron microscopy (SEM).

In a first embodiment hence, the superficial area of the nanoparticle agglomerate is in the range from 3 m² g⁻¹ to 10 m² g⁻¹ as measured with Brunauer-Emmett-Teller (BET) gas adsorption method by using powdered samples and a Sorpty 1750 (Carlo Erba, Milan Italy) and said nanoparticle agglomerate has preferably a spherical shape and a diameter in the range from 2 to 25 μm. All the instruments used for determining the diameter are instruments for scanning electron microscopy (SEM).

In a further and preferred aspect of the invention allows to obtain a fluorine-doped citrate-coated amorphous calcium phosphate nanoparticle by providing of adding a fluoride compound in the second solution of step 2).

Preferably the fluoride compound is a fluoride of a cation selected from the group consisting of sodium and potassium.

Therefore in another and preferred aspect the invention concerns a fluorine-doped citrate-coated amorphous calcium phosphate nanoparticle obtainable by the process according to the invention and comprising the addition of a fluoride compound in step 2), wherein the drying step 5) is a freeze-drying step, being said nanoparticle characterized by a superficial area from 250 m² g⁻¹ to 370 m² g⁻¹, preferably from 270 m² g⁻¹ to 370 m² g⁻¹, as measured with Brunauer-Emmett-Teller (BET) gas adsorption method and having a round shape with a diameter in the range from 30 to 80 nm as measured by transmission electron microscopy (TEM) images.

In a first embodiment hence, the superficial area of fluorine-doped citrate-coated amorphous calcium phosphate nanoparticle is in the range from 250 m² g⁻¹ to 370 m² g⁻¹, preferably from 270 m² g⁻¹ to 370 m² g⁻¹, as measured with Brunauer-Emmett-Teller (BET) gas adsorption method by using powdered samples and a Sorpty 1750 (Carlo Erba, Milan Italy) and said nanoparticle has preferably a spherical shape with a diameter in the range from 30 to 80 nm. All the instruments used for determining the diameter are instruments capable to have transmission electron microscopy (TEM) images.

In another and preferred aspect the invention concerns a fluorine-doped citrate-coated amorphous calcium phosphate nanoparticle agglomerate obtainable by the process according to the invention and comprising the addition of a fluoride compound in step 2), wherein the drying step 5) is a spray-drying step, being said nanoparticle agglomerate characterized by a superficial area from 3 m² g⁻¹ to 10 m² g⁻¹ as measured with Brunauer-Emmett-Teller (BET) gas adsorption method and having a round-shape with a diameter in the range from 2 to 25 μm as measured by scanning electron microscopy (SEM).

The superficial area is measured with Brunauer-Emmett-Teller (BET) gas adsorption method by using powdered samples and a Sorpty 1750 (Carlo Erba, Milan Italy).

In a further aspect the invention concerns the use of a particle of the invention as a biomaterial for use in dentistry applications. Preferably the biomaterial is used for the dental hard tissues remineralization or as dentin desensitizer, where in this latter case its action is preferably to fill and occlude the dentinal tubules.

In a still further aspect the invention concerns the use of a particle of the invention as a biomaterial in orthopaedic applications.

EXPERIMENTAL PART

Materials

Calcium chloride dihydrate ($CaCl_2.2H_2O$, ≥99.0% pure), sodium citrate tribasic dihydrate ($Na3(C6H5O7).2H_2O$, ≥99.0% pure (hereafter named Na3(Cit)), sodium phosphate dibasic dihydrate ($Na_2HPO_4.2H_2O$, ≥99.0% pure), strontium chloride hexahydrate ($SrCl2.6H2O$, ≥99.0% pure), magnesium chloride hexahydrate ($MgCl2.6H2O$, ≥99.0% pure), sodium carbonate monohydrate ($Na_2CO_3.2H_2O$, ≥99.0% pure), sodium fluoride (NaF, ≥99.0% pure), potassium chloride (KCl≥99.5% pure), potassium thiocyanate (KSCN≥98.0% pure), sodium carbonate monobasic ($NaHCO_3$, ≥99.7% pure) and lactic acid ($C_3H_6O_3$≥90.0% pure) were purchased from Sigma Aldrich (St. Luis, Mo., USA). All the solutions were prepared with ultrapure water (0.22 μS, 25° C., MilliQ©, Millipore).

Instruments and Methods of Evaluation

X-ray diffraction (XRD) patterns of the samples reported in Table 1 were recorded on a D8 Advance diffractometer (Bruker, Karlsruhe, Germany) equipped with a Lynx-eye position sensitive detector using Cu Kα radiation (λ=1.54178 Å) generated at 40 kV and 40 mA. Spectra were recorded in the 2θ range from 10 to 60° with a step size (2θ) of 0.021 and a counting time of 0.5 s.

Fourier transform infrared (FT-IR) spectroscopy analyses were carried out on a Nicolet 5700 spectrometer (Thermo Fisher Scientific Inc., Waltham, Mass., USA) with a resolution of 2 cm$^{-1}$ by accumulation of 64 scans covering the 4000 to 400 cm$^{-1}$ range, using the KBr pellet method.

Transmission electron microscopy (TEM) and selected area electron diffraction (SAED) evaluation was performed with Tecnai F20 microscope (Fei Corp., Hillsboro, Oreg., USA) operating at 120 kV. The powder samples were ultrasonically dispersed in ultrapure water and then a few droplets of the slurry were deposited on 200 mesh copper TEM grids covered with thin amorphous carbon films and incubated for several minutes.

Quantification of Ca and P, Mg, and Sr was carried out by inductively coupled plasma atomic emission (ICP-OES) spectrometer (Agilent Technologies 5100 ICP-OES, Santa Clara, Calif., USA) while F was quantified with a fluoride ion electrode (Intellical™ ISEF121, Hach Lange, Loveland, Colo., USA). Samples were prepared dissolving an aliquot of powder in a 1 wt. % $HNO_3$ solution.

Thermogravimetry analyses (TGA) were performed using a STA 449 Jupiter (Netzsch GmbH, Selb, Germany) apparatus. About 10 mg of sample was weighted in a platinum crucible and heated from room temperature to 1200° C. under air flow with a heating rate of 10° C./min.

thermostated at 4° C. and then freeze-dried overnight at −50° C. under a vacuum of 3 mbar.

F-ACP samples were prepared similarly to ACP while 50 mM $NaF_2$ was added to the solution (ii).

Example 2

Preparation of the Nanoparticle of the Invention

Following the same preparation of example 1, samples of ACP and F-ACP (doped using 50 mM $NaF_2$) were also prepared decreasing the initial molar Cit/Ca ratio to 2 and 1 (hereafter coded as $ACP^2$, $F-ACP^2$ and $ACP^1$, $F-ACP^1$, respectively).

Example 2Bis

Preparation of the Nanoparticle of the Invention with Mg and Sr

Following the preparation of example 2, samples of SrF-ACP, MgF-ACP and SrMgF-ACP were also prepared similarly to F-ACP while 5 mM $SrCl_2$ or 40 mM $MgCl_2$ or both were added to the solution (i). The initial molar Cit/Ca ratio of 2 and 1 (hereafter coded as $SrF-ACP^2$, $MgF-ACP^2$, $SrMgF-ACP^2$ and $SrF-ACP^1$, $MgF-ACP^1$, $SrMgF-ACP^1$, respectively) was used.

Codes of the samples and concentration of the chemical reactants used for the preparation of example 1 and example 2 are reported in the following Table 1.

TABLE 1

| Sample | Cit/Ca | NaF (mM) | $CaCl_2$ (mM) | $Na_3$(Cit) (mM) | $Na_2HPO_4$ (mM) | $Na_2CO_3$ (mM) | $MgCl_2$ (mM) | $SrCl_2$ (mM) |
|---|---|---|---|---|---|---|---|---|
| $ACP^4$ | 4 | — | 100 | 400 | 120 | 200 | — | — |
| $F-ACP^4$ | 4 | 50 | 100 | 400 | 120 | 200 | — | — |
| $ACP^2$ | 2 | — | 100 | 200 | 120 | 200 | — | — |
| $F-ACP^2$ | 2 | 50 | 100 | 200 | 120 | 200 | — | — |
| $ACP^1$ | 1 | — | 100 | 100 | 120 | 200 | — | — |
| $F-ACP^1$ | 1 | 50 | 100 | 100 | 120 | 200 | — | — |
| $SrF-ACP^2$ | 2 | 50 | 100 | 200 | 120 | 200 | — | 5 |
| $MgF-ACP^2$ | 2 | 50 | 100 | 200 | 120 | 200 | 40 | — |
| $SrMgF-ACP^2$ | 2 | 50 | 100 | 200 | 120 | 200 | 40 | 5 |
| $SrF-ACP^1$ | 1 | 50 | 100 | 100 | 120 | 200 | — | 5 |
| $MgF-ACP^1$ | 1 | 50 | 100 | 100 | 120 | 200 | 40 | — |
| $SrMgF-ACP^1$ | 1 | 50 | 100 | 100 | 120 | 200 | 40 | 5 |

Brunauer-Emmett-Teller (BET) gas adsorption method was employed to measure the specific surface area (SSA) of powdered samples using a Sorpty 1750 (Carlo Erba, Milan Italy).

Scanning electron microscopy (SEM) evaluation was performed employing a Sigma NTS Gmbh (Carl Zeiss, Oberkochen, Germany). The powder samples were mounted on aluminum stubs using carbon tape, and prior the analyses sputter coated with gold in a Sputter Coater E5100 (Polaron Equipment, Watford, Hertfordshire, UK) under argon at $10^{-3}$ mbar for 4 minutes with a sputtering current of 30 mA.

Example 1

Preparation of the Nanoparticle of the Prior Art WO2016/016012452

Dry powder ACP (amorphous calcium phosphate) was synthesized by mixing two solutions (1:1 v/v, 200 ml total) at room temperature of (i) 100 mM $CaCl_2$)+400 mM $Na_3$(Cit) and (ii) 120 mM $Na_2HPO_4$+200 mM $Na_2CO_3$. The pH was adjusted to 8.5 with HCl solution. When the mixture became milky, the particles were washed three times with ultrapure water by centrifugation at 5000 rpm for 15 min The samples of the prior art have a molar ratio between citrate and calcium of 4, while the samples of the present invention were prepared with a molar ratio in the range from 1 to 2.

Example 3: Evaluation of the Physical Characteristics and of the Compositions of the Particles of $ACP^4$ Prepared in Example 1

Dry powder $ACP^4$ prepared in example 1 was evaluated for physical properties with the instruments above reported.

In FIG. 1A TEM micrograph of $ACP^4$ is reported, revealing round shaped nanoparticles rather than faceted and angular shape typical of crystalline CaP, with sizes ranging between 20 and 50 nm. The SAED pattern collected for such nanoparticles (top right inset in FIG. 1A) demonstrates their amorphous nature due to the presence of diffuse wings rather than spots.

Figure 1B:
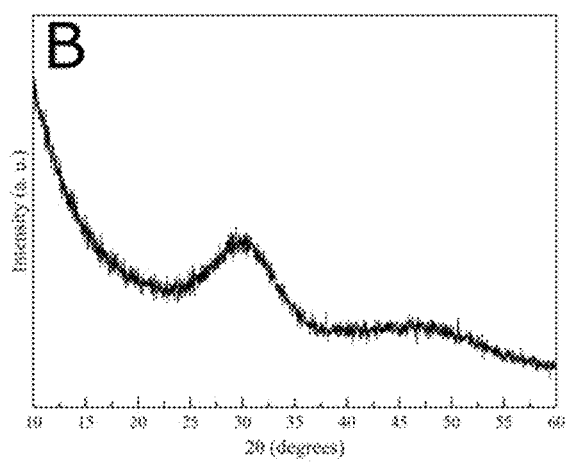
FIG. 1B shows XRD patterns of $ACP^4$ prepared in example 1.
Figure 1C:
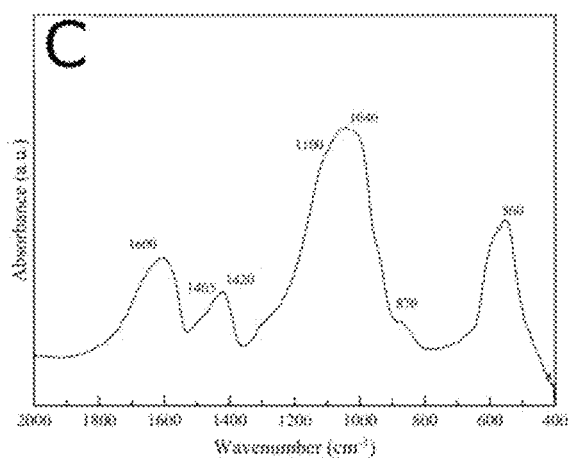
FIG. 1C shows FT-IR spectra of $ACP^4$ prepared in example 1.

XRD pattern of $ACP^4$ (FIG. 1B) reveals a broad band at about 30° (2θ) typical of a phase without a long range periodic regularity confirming the non-crystalline structure of $ACP^4$ and excluding the presence of HA and others CaP crystalline phases. FT-IR spectrum (FIG. 1C) displays broad, unresolved bands characteristic of CaP having amorphous structure. In particular, the adsorption bands at about 560 and 1050 cm$^{-1}$ were associated to the bending and stretching modes of phosphate groups, respectively; those at about 870 cm$^{-1}$ and in the range 1400-1500 cm$^{-1}$ were attribute to the carbonate ions, while the band at about 1605 cm$^{-1}$ was assigned to the adsorbed water as well as the stretching of COO$^-$ of citrate. Therefore, FIGS. 1A, 1B, 1C confirmed the spherical shape of nanoparticles made of amorphous calcium phosphate.

Example 4: Evaluation of the Physical Characteristics and of the Compositions of the Particles of F-ACP Prepared in Example 1

Figure 2A:
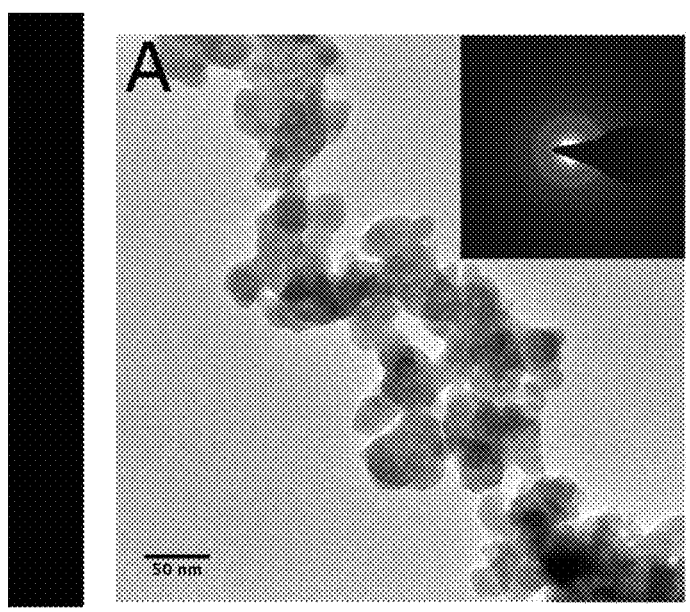
FIG. 2A shows TEM micrograph of $F-ACP^4$ prepared in example 1; (inset: corresponding SAED pattern)
Figure 2B:
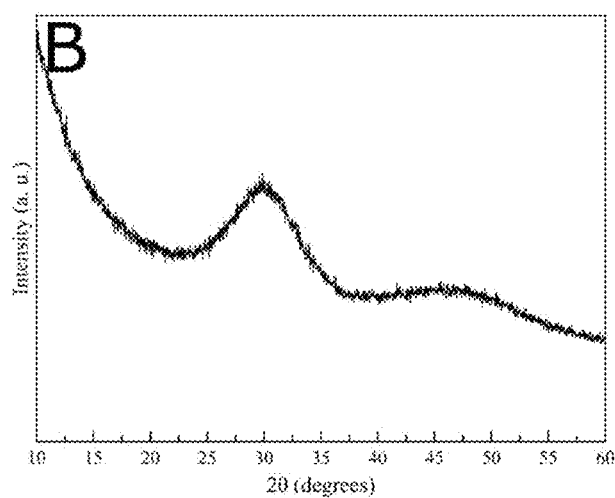
FIG. 2B shows XRD pattern of $F-ACP^4$ prepared in example 1.
Figure 2C:
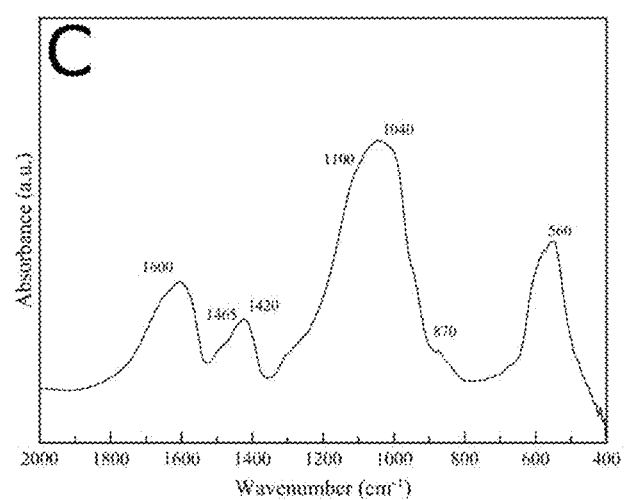
FIG. 2C shows FT-IR spectra of $F-ACP^4$ prepared in example 1.

With reference to example 1, in a first step the reagents concentration as well as the Cit/Ca ratio were kept constant respect to the protocol used for the preparation of ACP$^4$, while NaF was added to dope ACP$^4$ (hereafter called F-ACP$^4$)). TEM image of F-ACP$^4$ (FIG. 2A) displays round shaped particles having size and morphology similar to that of ACP$^4$. The SAED pattern collected for such nanoparticles (top right inset in FIG. 2A) demonstrates their amorphous nature due to the presence of diffuse wings rather than spots. XRD patterns of F-ACP$^4$ (FIG. 2B) show the same broad diffraction peak at about 30° (2θ) of that recorded for ACP$^4$ indicating that the presence of F$^-$ ions did not cause the precipitation of fluoride salt or other crystalline CaP phases. FT-IR spectra of F-ACP$^4$ also display broad, unresolved bands similar to those reported in the FT-IR spectrum of ACP$^4$ (FIG. 2C).

ACP$^2$ and ACP$^1$, and these samples were called F-ACP$^2$ and F-ACP$^1$ respectively.

Figure 3A:
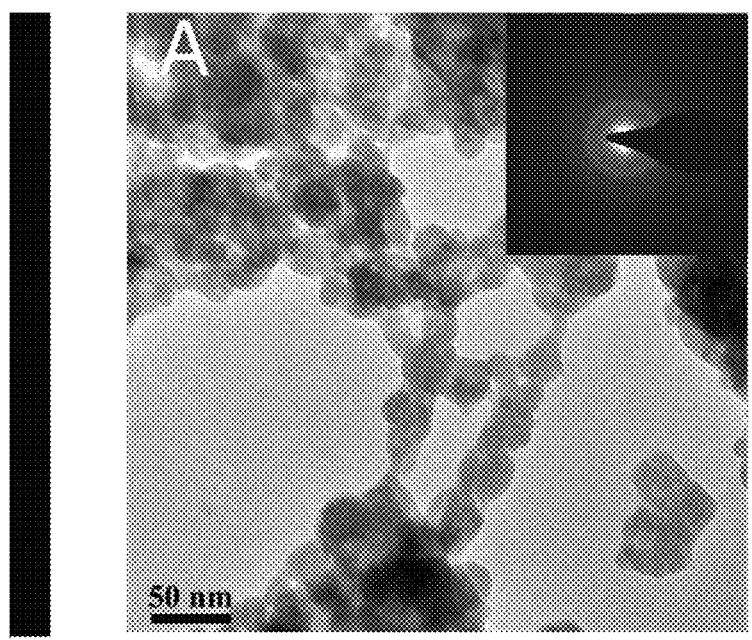
FIG. 3A shows TEM micrograph of $ACP^1$, prepared in example 2; (inset: corresponding SAED pattern)
Figure 3B:
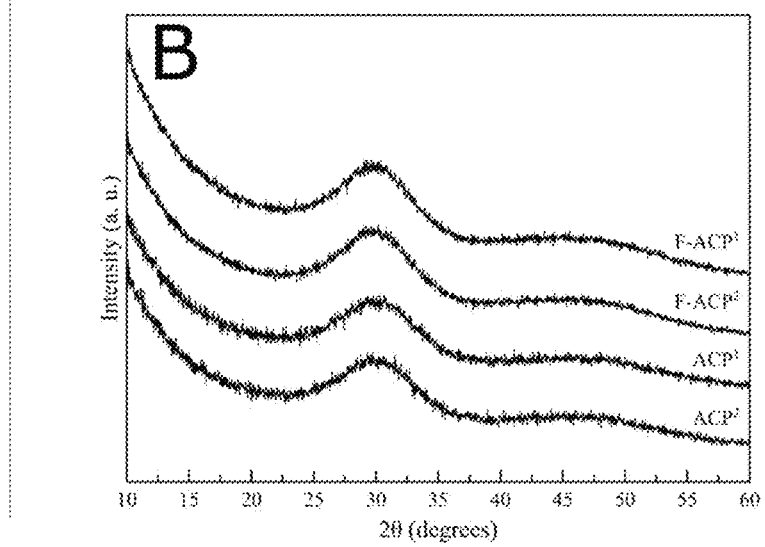
FIG. 3B shows XRD patterns of $ACP^2$, $ACP^1$, $F-ACP^1$, $F-ACP^2$ prepared in example 2.
Figure 3C:
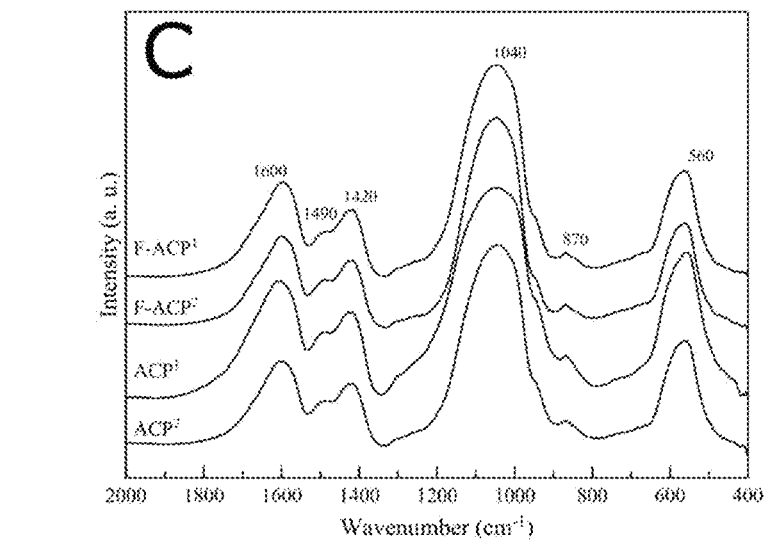
FIG. 3C shows FT-IR spectra of $ACP^2$, $ACP^1$, $F-ACP^1$, $F-ACP^2$ prepared in example 2.

TEM images of ACP$^2$ (not shown) and ACP$^1$ (FIG. 3A) display round shaped particles having size and shape comparable to ACP$^4$. The SAED pattern collected for ACP$^1$ (top right inset in FIG. 3A) demonstrates their amorphous nature due to the presence of diffuse wings rather than spots. Also in this case the addition of F$^-$ did not induce changes in the size and morphology in comparison to the un-doped counterparts. The XRD patterns of ACP$^2$, ACP$^1$, F-ACP$^2$ and F-ACP$^1$ (FIG. 3B) showed the same broad diffraction band characteristic of a pure amorphous phase. FT-IR spectra of ACP$^2$, ACP$^1$, F-ACP$^2$ and F-ACP$^1$ (FIG. 3C) also displayed broad, unresolved bands similar to those reported in the other FT-IR spectra.

The particles of ACP or F-ACP according to the invention hence were round shaped and had dimensions similar to those of the prior art.

Example 5 Bis

Figure 8:
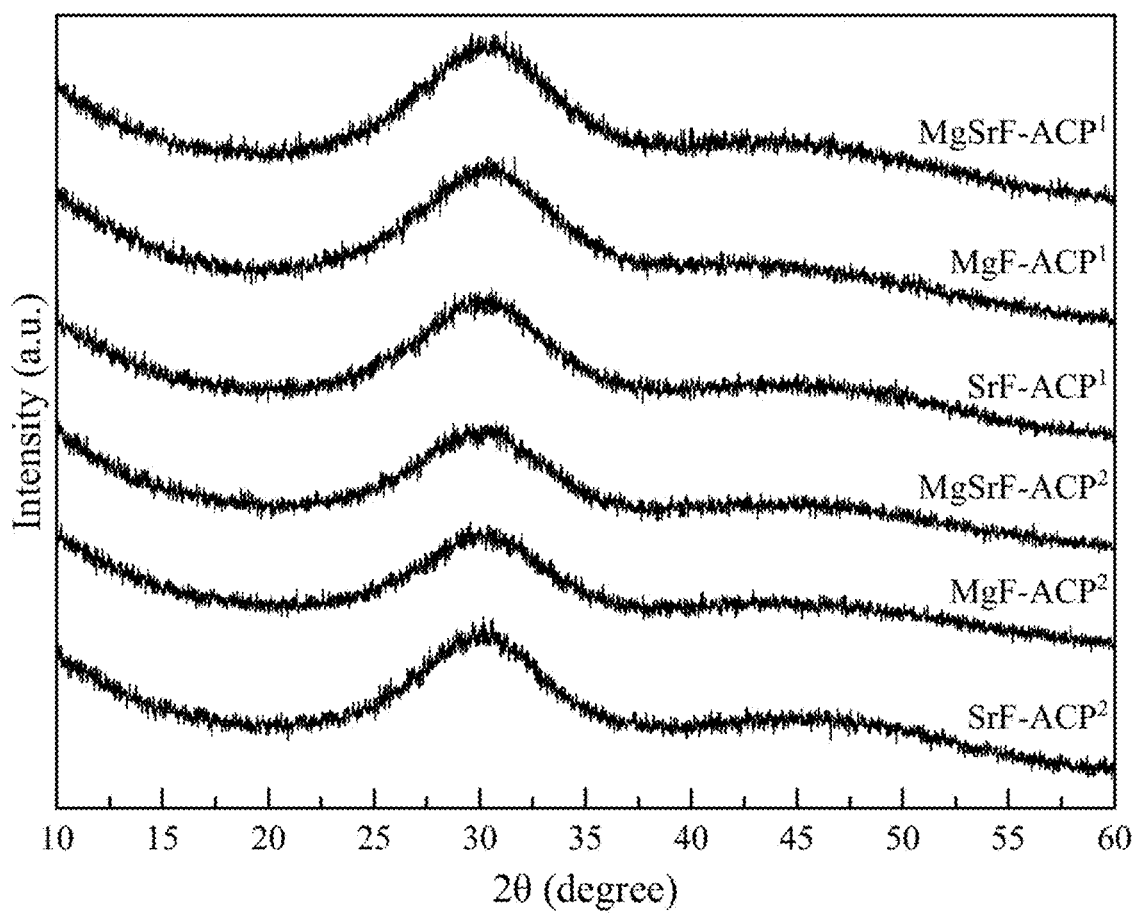
FIG. 8 shows XRD patterns of $SrF-ACP^2$, $MgF-ACP^2$, $SrMgF-ACP^2$, $SrF-ACP^1$, $MgF-ACP^1$, $SrMgF-ACP^1$ prepared in example 2bis.
Figure 9:
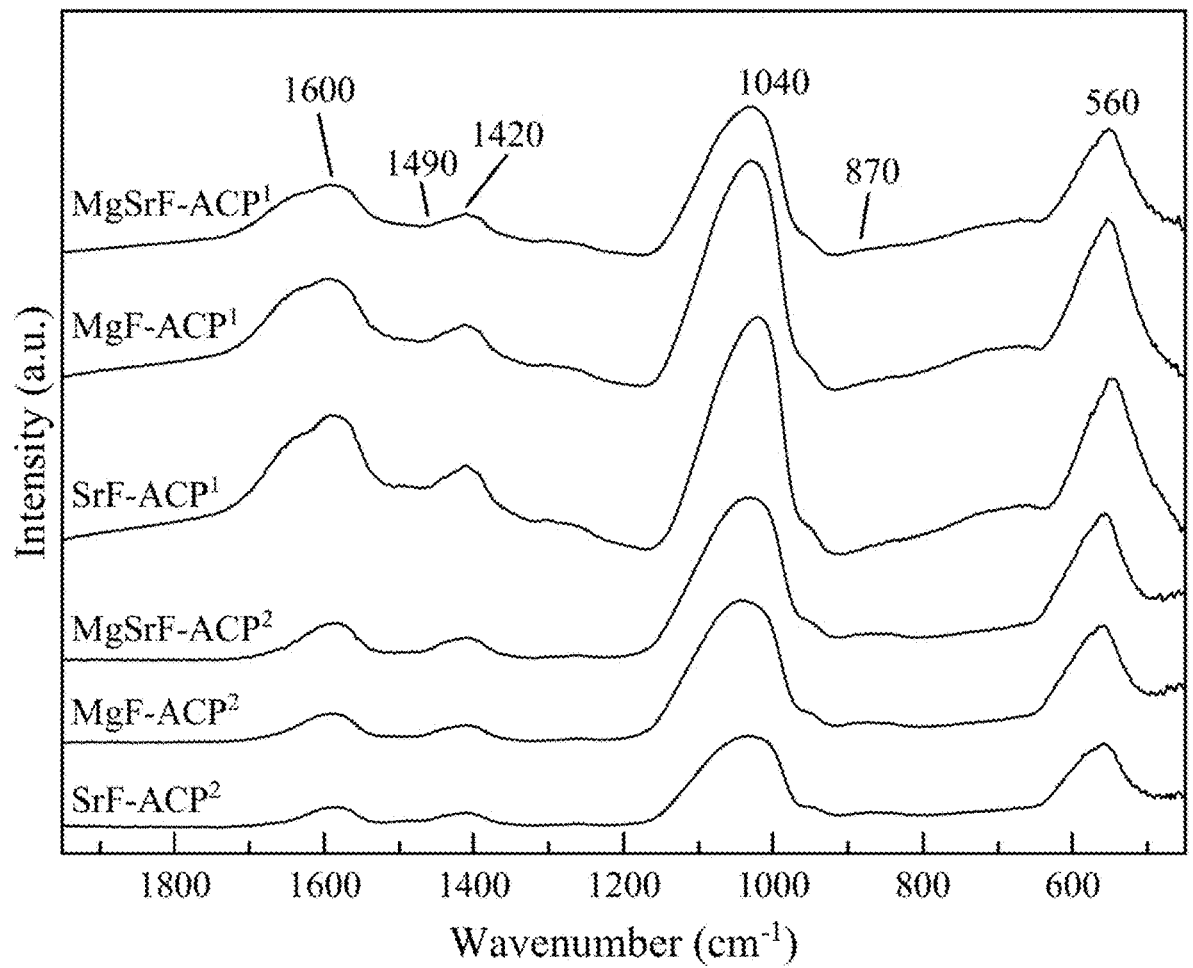
FIG. 9 shows FT-IR spectra of $SrF-ACP^2$, $MgF-ACP^2$, $SrMgF-ACP^2$, $SrF-ACP^1$, $MgF-ACP^1$, $SrMgF-ACP^1$ prepared in example 2bis.

The XRD patterns of SrF-ACP$^2$, MgF-ACP$^2$, SrMgF-ACP$^2$, SrF-ACP$^1$, MgF-ACP$^1$, SrMgF-ACP$^1$ (FIG. 8) showed the same broad diffraction band characteristic of a pure amorphous phase. FT-IR spectra of SrF-ACP$^2$, MgF-ACP$^2$, SrMgF-ACP$^2$, SrF-ACP$^1$, MgF-ACP$^1$, SrMgF-ACP$^1$ (FIG. 9) also displayed broad, unresolved bands similar to those reported in the other FT-IR spectra.

Example 6: Chemical Composition of Samples Prepared in Example 1 and Example 2 and Example 2Bis The chemical composition of the samples prepared in example 2 are summarized in Table 2.

TABLE 2

| Sample | Ca$^a$ (wt %) | P$^a$ (wt %) | Calcium + Strontium + Magnesium/ Phosphate$^a$ (mol) | F$^b$ (wt %) | Mg$^a$ (wt %) | Sr$^a$ (wt %) | Citrate$^c$ (wt %) | Carbonate$^c$ (wt %) | SSA$_{BET}$$^d$ (m$^2$g$^{-1}$) |
|---|---|---|---|---|---|---|---|---|---|
| ACP$^2$ | 29.1 ± 1.0 | 13.2 ± 0.3 | 1.70 ± 0.02 | — | | | 2.2 ± 0.2 | 3.8 ± 0.4 | 287 ± 29 |
| F-ACP$^2$ | 32.1 ± 0.5 | 13.1 ± 0.2 | 1.89 ± 0.01 | 2.2 ± 0.1 | | | 2.0 ± 0.2 | 3.4 ± 0.3 | 328 ± 33 |
| ACP$^1$ | 28.0 ± 0.6 | 12.7 ± 0.2 | 1.70 ± 0.04 | — | | | 1.8 ± 0.2 | 3.2 ± 0.3 | 309 ± 31 |
| F-ACP$^1$ | 31.9 ± 0.8 | 13.1 ± 0.3 | 1.88 ± 0.01 | 1.8 ± 0.1 | | | 2.4 ± 0.2 | 3.1 ± 0.3 | 293 ± 29 |
| SrF-ACP$^2$ | 29.4 ± 0.1 | 12.9 ± 0.1 | 1.86 ± 0.02 | 2.5 ± 0.1 | — | 3.8 ± 0.1 | 2.3 ± 0.2 | 3.4 ± 0.3 | 287 ± 29 |
| MgF-ACP$^2$ | 27.3 ± 0.4 | 14.2 ± 0.2 | 1.82 ± 0.01 | 3.4 ± 0.1 | 3.7 ± 0.1 | — | 2.1 ± 0.2 | 3.2 ± 0.3 | 289 ± 29 |
| SrMgF-ACP$^2$ | 25.3 ± 0.3 | 13.2 ± 0.2 | 1.86 ± 0.03 | 4.1 ± 0.1 | 3.1 ± 0.1 | 3.6 ± 0.1 | 2.4 ± 0.2 | 3.5 ± 0.3 | 273 ± 27 |
| SrF-ACP$^1$ | 30.0 ± 0.9 | 13.4 ± 0.4 | 1.83 ± 0.01 | 2.2 ± 0.1 | — | 3.6 ± 0.1 | 2.2 ± 0.2 | 3.3 ± 0.3 | 352 ± 35 |
| MgF-ACP$^1$ | 26.7 ± 0.1 | 14.2 ± 0.1 | 1.80 ± 0.01 | 3.7 ± 0.1 | 3.8 ± 0.1 | — | 2.3 ± 0.2 | 3.6 ± 0.3 | 304 ± 30 |
| SrMgF-ACP$^1$ | 24.8 ± 0.2 | 13.7 ± 0.1 | 1.81 ± 0.01 | 3.7 ± 0.1 | 3.6 ± 0.1 | 3.1 ± 0.2 | 1.9 ± 0.2 | 3.4 ± 0.3 | 318 ± 32 |

$^a$Quantified by ICP-OES;
$^b$Quantified by fluoride ion electrode;
$^c$Quantified by TGA;
$^d$Calculated from BET adsorption.

Example 5: Evaluation of the Physical Characteristics and of the Compositions of the Particles of ACP and F-ACP Prepared in Example 2

As above reported, two ACP samples were prepared changing the nominal Cit/Ca ratio of the reagents according to the invention, that was set to 4 according to the prior art, to 2 or 1 (hereafter called ACP$^2$ and ACP$^1$, respectively) according to the invention in order to evaluate the effect of the molar ratio Cit/Ca on the chemical-physical features of these amorphous materials. Moreover, the same amount of NaF used for the synthesis of F-ACP$^4$ was employed to dope The SSA$_{BET}$ was determined also for the sample of prior art as prepared in example 1.

The following values were obtained:
ACP$^4$ 200±20 m$^2$ g$^{-1}$
F-ACP$^4$ 213±21 m$^2$ g$^{-1}$ The value of SSA$_{BET}$ resulted to be a feature differentiating the ACP and F-ACP obtained with the process of the prior art and the process of the invention.

TGA curve of the samples according to the invention mainly exhibits four weight losses, that can be attributed to adsorbed water (from room temperature to 150° C.), structural water (from 150 to 350° C.), citrate (from 350 to 700° C.) and carbonate (from 700 to 1000° C.). According to these losses the content of citrate and carbonate were estimated and reported in Table 2.

The calcium/phosphate ratio of $ACP^2$ was similar to $ACP^1$ while $F-ACP^2$ and $F-ACP^1$ show higher calcium contents and higher Ca/P ratios than their undoped counterparts. The calcium/phosphate ratio of $F-ACP^2$ was similar to $F-ACP^1$.

The calcium+strontium+magnesium/phosphate ratio of $SrF-ACP^2$, $MgF-ACP^2$, $SrMgF-ACP^2$, $SrF-ACP^1$, $MgF-ACP^1$, $SrMgF-ACP^1$ was similar to the value calculated for the samples $F-ACP^2$ and $F-ACP^1$. The content of citrate and carbonate didn't change among the samples doped with Sr and Mg and it was similar to value calculated for the samples $F-ACP^2$ and $F-ACP^1$. Interestingly, it was found that when Mg, alone or in combination with Sr, is included in the preparation, the amount of fluoride increased.

Without being bound to any theory the inventors deem that the higher surface areas were due to the process of the invention which provides for the molar ratio of citrate ion to calcium ion in the range from 1 to 2.

The above data demonstrate that the citrate-coated particles and fluorine-doped citrate-coated particles obtained by the process of the invention are different and so novel from the fluorine-doped citrate-coated particles of WO2016/012452.

Example 7: Ion Release in Artificial Saliva of Samples Prepared in Example 1 and Example 2

The application of ACP in tooth treatment products is based on the principle of releasing calcium and phosphate ions in order to generate a local supersaturation for triggering the enamel remineralization. Therefore, this effect has been tested in vitro. The in vitro ion release in acidic artificial saliva (a solution that mimics the human saliva after eating, without its macromolecular components) has been tested.

200 mg of ACP or F-ACP powders prepared in the examples 1 and 2 were dispersed into 10 mL of artificial saliva prepared as modified Tani-Zucchi solution containing KCl 20 mM, KSCN 5.3 mM, $Na_2HPO_4$ 1.4 mM, $NaHCO_3$ 15 mM, and lactic acid 10 mM. The suspension was maintained at 37° C. under shaking. At scheduled times, 8 ml of the supernatant (that was well separated from the solid phase by centrifugation at 5000 rpm for 15 min) was removed for $Ca^{2+}$ and $F^-$ quantification by ICP-OES and fluoride ion electrode, respectively. After that, samples were rinsed with 8 ml of fresh artificial saliva and the suspension was maintained at 37° C. under shaking and treated as previously described at the next time point.

Figure 4A:
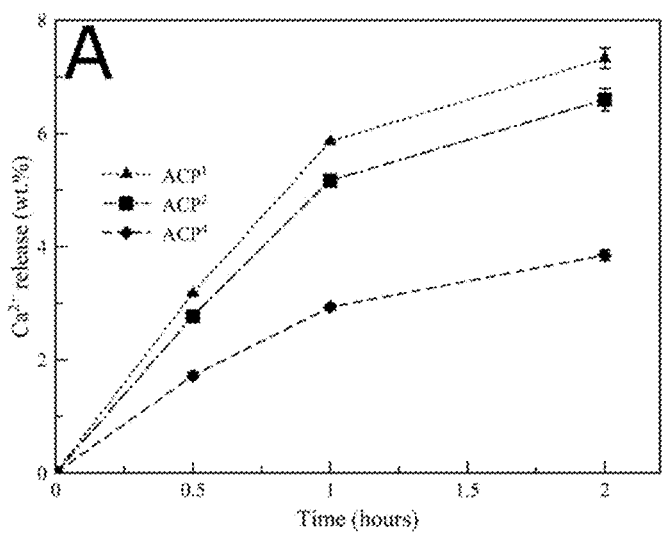
FIG. 4A reports cumulative $Ca^{2+}$ release from ACP samples prepared in example 1 and example 2; data are expressed as mean±standard deviation (n=5)
Figure 4B:
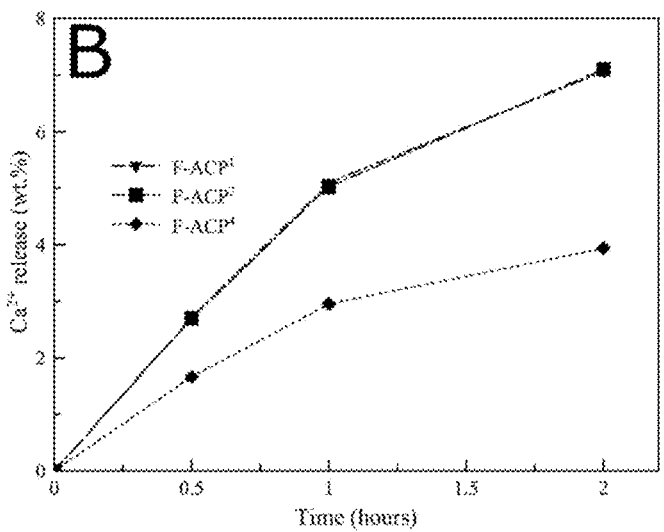
FIG. 4B reports cumulative $Ca^{2+}$ release from F-ACP samples prepared in example 1 and example 2; data are expressed as mean±standard deviation (n=5)
Figure 4C:
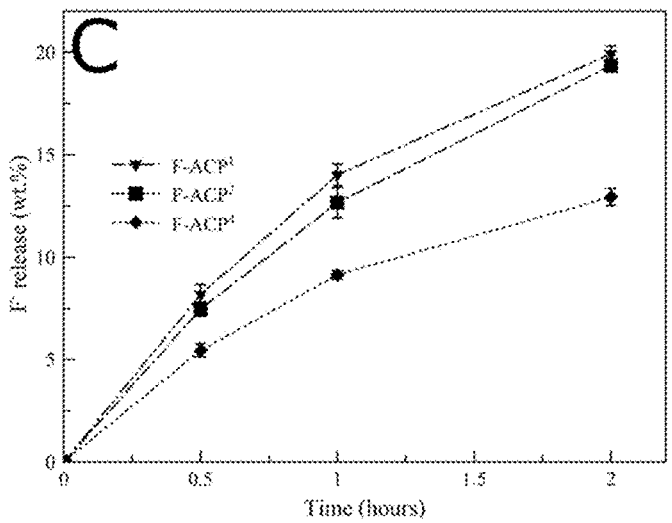
FIG. 4C reports cumulative $F^-$ from F-ACP samples prepared in example 1 and example 2; data are expressed as mean±standard deviation (n=5)

All the samples of examples 1 and 2 show a sustained release of $Ca^{2+}$ and $F^-$ ions in the first two hours (FIG. 4). The samples with a Cit/Ca ratio according to the invention showed surprisingly higher ion release rates, thus revealing themselves as an improved and advantageous product with respect to the prior art.

Without being bound to any theory the inventors deem that this surprising effect was probably due by the peculiar features of the particles of the invention that had higher surface areas, due to the specific molar ratio used in the process for producing the nanoparticles.

Example 7Bis

The in vitro ion release in acidic artificial saliva of $SrF-ACP^2$, $MgF-ACP^2$, $SrMgF-ACP^2$, $SrF-ACP^1$, $MgF-ACP^1$, $SrMgF-ACP^1$ prepared according to example 2bis has been tested in the same conditions of Example 7.

Figure 10A:
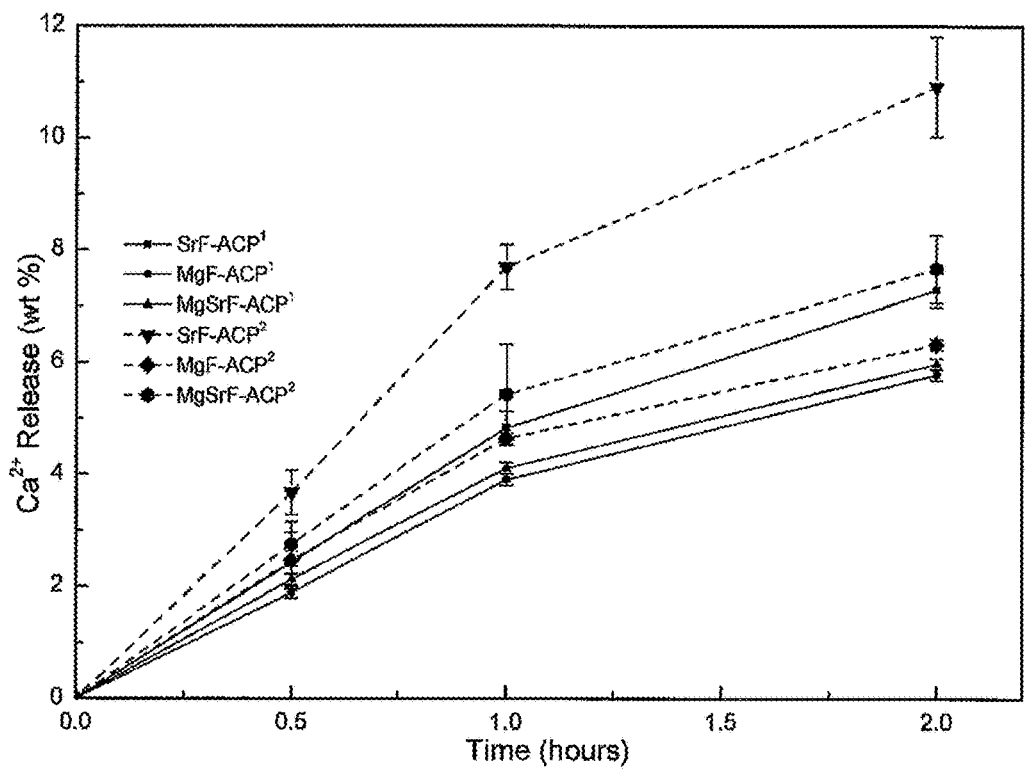
FIG. 10A reports cumulative $Ca^{2+}$ release from $SrF-ACP^2$, $MgF-ACP^2$, $SrMgF-ACP^2$, $SrF-ACP^1$, $MgF-ACP^1$, $SrMgF-ACP^1$ samples prepared in example 2bis; data are expressed as mean±standard deviation (n=5)
Figure 10B:
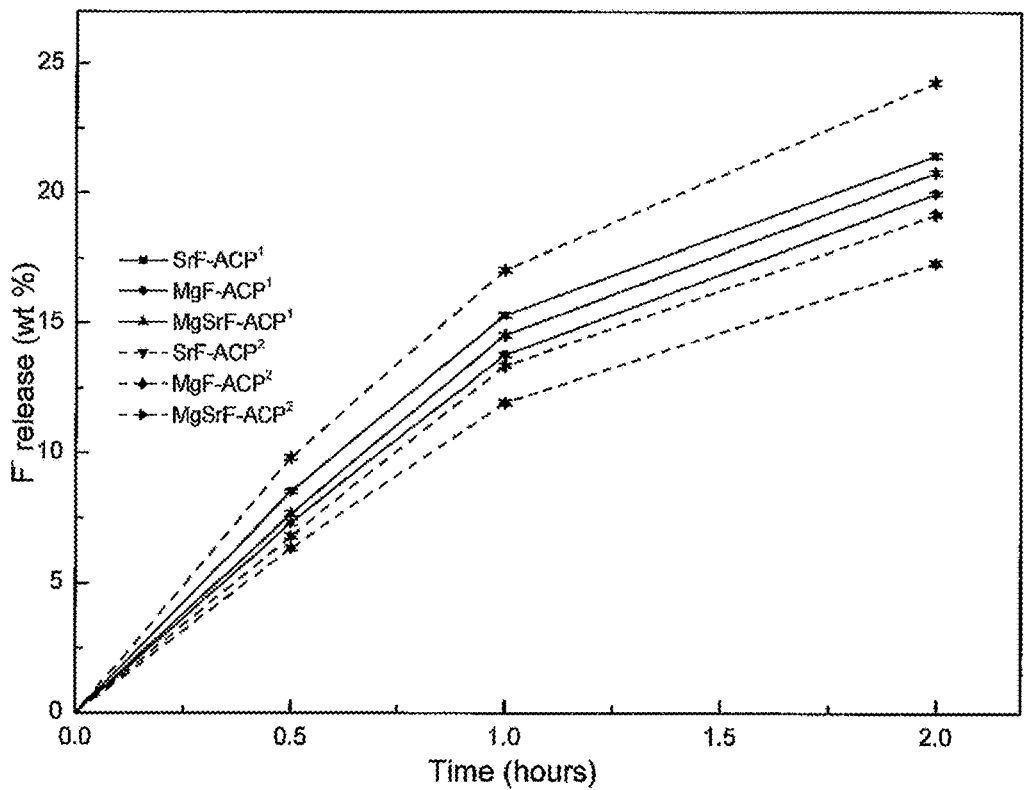
FIG. 10B reports cumulative $F^-$ release from $SrF-ACP^2$, $MgF-ACP^2$, $SrMgF—SrF-ACP^1$, $MgF-ACP^1$, $SrMgF-ACP^1$ samples prepared in example 2bis; data are expressed as mean±standard deviation (n=5).

All the samples of the example 2bis, similar to those of the examples 1 and 2, show a sustained release of $Ca^{2+}$ and $F^-$ ions in the first two hours (FIGS. 10A and 10B). The samples of the example 2bis according to the invention showed ion release rates comparable to the samples of the example 2, thus revealing themselves as an improved and advantageous product with respect to the prior art.

Example 8: Preparation of the Nanoparticle of the Invention Agglomerated in Microparticles (Nanoparticle Agglomerate of the Invention)

Figure 5:
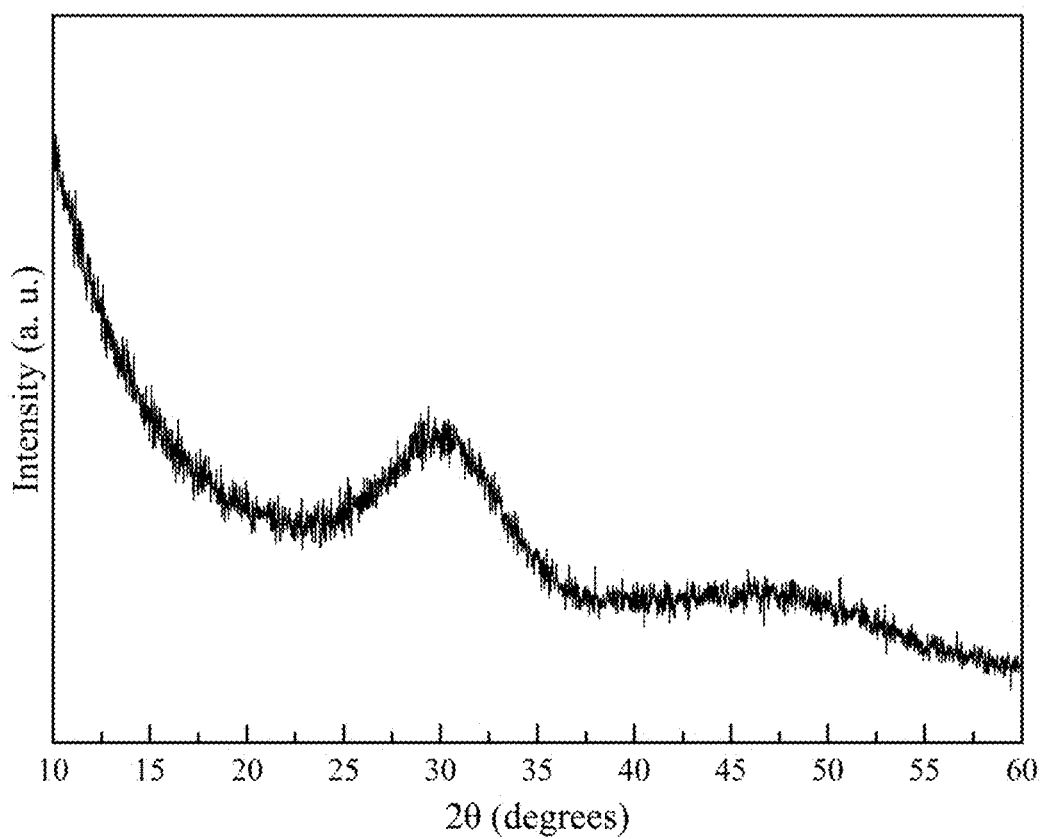
FIG. 5 shows XRD pattern of spray dried $F-ACP^1$ of example 8.
Figure 6:
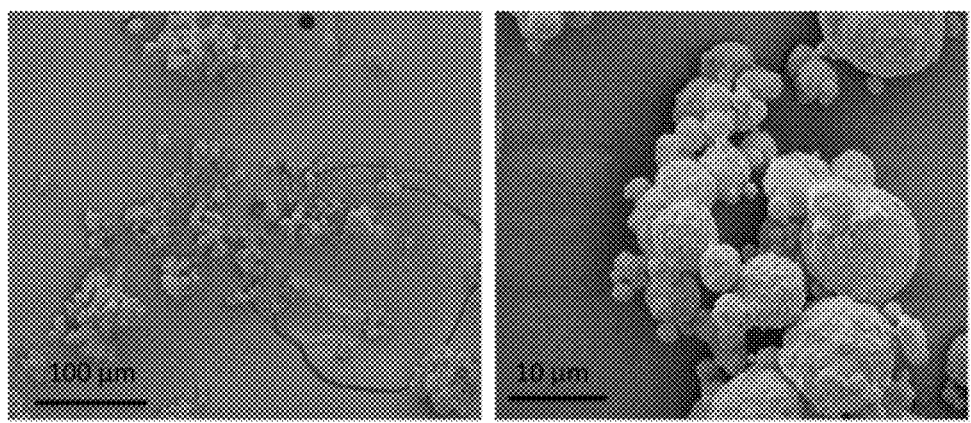
FIG. 6 shows SEM micrographs at different magnification of spray dried $F-ACP^1$ of example 8.

To evaluate the feasibility to dry the samples of example 2 by a spray dryer without affecting their amorphous feature, $ACP^2$, $ACP^1$, $F-ACP^2$ and $F-ACP^1$ after washings and as obtained in Example 2 have been re-suspended in water at 3.5% w/v and dried by spray drying (Mini Spray Dryer B-290, Büchi Labortechnik AG, Switzerland) under the following conditions: nozzle diameter 0.7 mm, feed rate 3 ml/min, argon flow rate 450 I $h^{-1}$, inlet temperature 120° C. and aspirator rate 70%. XRD pattern of the spray dried $F-ACP^1$ powder (FIG. 5) showed only a broad band at about 30° (2θ), corroborating the fact that the amorphous phase is preserved. SEM micrographs of the spray dried $F-ACP^1$ powder (FIG. 6) revealed that the sample consists of spherical particles of about 2-25 μm of diameter that in turn are composed of the agglomerated nanoparticles independently of the Cit/Ca ratio and presence of fluoride. The value of $SSA_{BET}$ of the dried powder was in the range 3-10 $m^2$ $g^{-1}$ independently of the Cit/Ca ratio and presence of fluoride.

Example 9: Dry Powder Stability of Samples Prepared in Example 2

Figure 7:
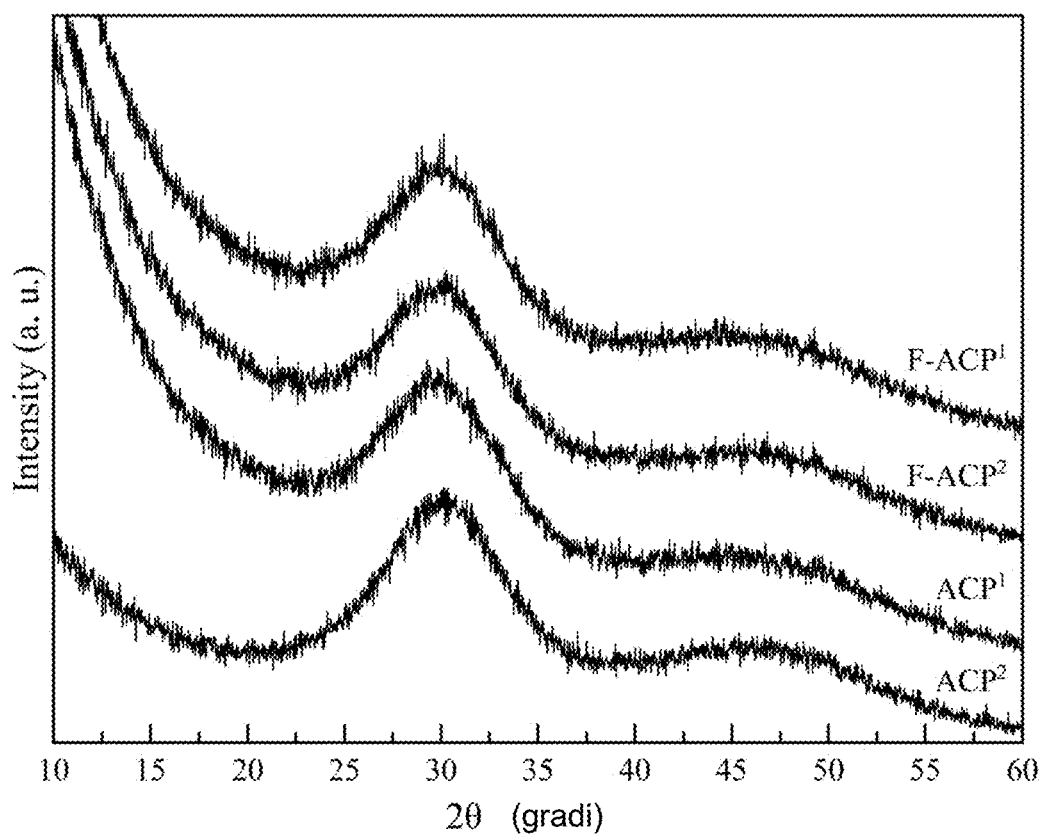
FIG. 7 shows XRD patterns of $ACP^2$, $ACP^1$, $F-ACP^2$, $F-ACP^1$ prepared in example 2, one year after synthesis, stored at room temperature of example 9.

ACP is unstable than the crystalline polymorphs of CaP, so it converts in the crystalline phase even in dry state reacting with atmospheric water. Therefore its use and handling is difficult unless a stable material is developed. The stability of $ACP^2$, $ACP^1$, $F-ACP^2$ and $F-ACP^1$ powders stored at room temperature has been evaluated analyzing its structure by collecting XRD up to one year (FIG. 7). Interestingly, the XRD pattern remained unchanged, establishing that the amorphous nature of all the samples is preserved during this period of time.

The invention claimed is:

1. A process for the preparation of a citrate-coated amorphous calcium phosphate nanoparticle which comprises the following steps:
   1) providing a first solution of a salt of calcium and a citrate salt wherein the molar ratio of citrate ion to calcium ion is in the range from 1 to 2 thus obtaining a clear first solution;
   2) providing a second solution of a salt capable to give phosphate anion and a carbonate salt;
   3) mixing together the clear first solution and the second solution at a pH in the range from 8 to 11;
   4) precipitating the nanoparticle; and
   5) drying the nanoparticle obtained from step 4).

2. The process according to claim 1, wherein the salt of calcium is made of an anion selected from the group consisting of chloride, nitrate, hydroxide, acetate, oxalate, lactate.

3. The process according to claim 1, wherein the salt of citrate is made of a cation selected from the group consisting of sodium and potassium.

4. The process according to claim 1, wherein the molar ratio of citrate ion to calcium ion is about 2.

5. The process according to claim 1, wherein the first solution of step 1) comprises at least one further salt selected from the group of: strontium salt, and magnesium salt.

6. The process according to claim 1, wherein the salt capable to give phosphate anion is a salt of phosphate, hydrogen phosphate or hydrogen phosphate.

7. The process according to claim 1, wherein the pH of step 3) is in the range from 8.5-10.7.

8. The process according to claim 1, wherein in the mixing step 3) the second solution is added to the clear first solution.

9. The process according to claim 1, wherein in step 4) the precipitation is carried out by providing sedimentation cycles by centrifugation removal of supernatant, collecting and washing the precipitate.

10. The process according to claim 1, wherein the drying step 5) is selected from freeze-drying, spray-drying and ventilated oven drying.

11. The process according to claim 1, wherein in step 1) a fluoride compound is added.

12. The process according to claim 11, wherein the fluoride compound is a fluoride of a cation selected from the group consisting of sodium and potassium.

13. A citrate-coated amorphous calcium phosphate nanoparticle obtainable by the process according to claim 1, wherein the drying step 5) is a freeze-drying step, being said nanoparticle characterized by a superficial area from 250 m2g−1 to 360 m2g−1 as measured with Brunauer-Emmett-Teller (BET) gas adsorption method and having a round-shaped morphology with a diameter in the range from 30 to 80 nm as measured by transmission electron microscopy (TEM) images.

14. A citrate-coated amorphous calcium phosphate nanoparticle agglomerate obtainable by the process according to claim 1, wherein the drying step 5) is a spray-drying step, being said nanoparticle agglomerate characterized by a superficial area from 2 m2g−1 to 10 m2g−1 as measured with Brunauer-Emmett-Teller (BET) gas adsorption method and having a round shaped morphology with a diameter in the range from 2 to 25 μm as measured by scanning electron microscopy (SEM).

15. A fluorine-doped citrate-coated amorphous calcium phosphate nanoparticle obtainable by the process according to claim 1, wherein the drying step 5) is a freeze-drying step, being said nanoparticle characterized by a superficial area from 250 m2g−1 to 370 m2g−1 as measured with Brunauer-Emmett-Teller (BET) gas adsorption method and having a round shaped morphology with a diameter in the range from 30 to 80 nm as measured by transmission electron microscopy (TEM) images.

16. A fluorine-doped citrate-coated amorphous calcium phosphate nanoparticle agglomerate obtainable by the process according to claim 1, wherein the drying step 5) is a spray-drying step, being said nanoparticle agglomerate characterized by a superficial area from 3 m2g−1 to 10 m2g−1 as measured with Brunauer-Emmett-Teller (BET) gas adsorption method and having a round shape morphology with a diameter in the range from 2 to 25 μm as measured by scanning electron microscopy (SEM).

17. A dentistry application method comprising applying to the surface of a tooth a biomaterial including nanoparticles according to claim 13.

18. The dentistry application method according to claim 17, further comprising remineralizing a dental hard tissue of the tooth or desensitizing dentin of the tooth with the biomaterial.

19. A dentistry application method comprising applying to the surface of a tooth a biomaterial including nanoparticles according to claim 14.

20. The dentistry application method according to claim 19, further comprising remineralizing a dental hard tissue of the tooth or desensitizing dentin of the tooth with the biomaterial.

21. A dentistry application method comprising applying to the surface of a tooth a biomaterial including nanoparticles or a nanoparticle agglomerate according to claim 15.

22. The dentistry application method according to claim 21, further comprising remineralizing a dental hard tissue of the tooth or desensitizing dentin of the tooth with the biomaterial.

23. A dentistry application method comprising applying to the surface of a tooth a biomaterial including nanoparticles.

24. The dentistry application method according to claim 23, further comprising remineralizing a dental hard tissue of the tooth or desensitizing dentin of the tooth with the biomaterial.

25. The process according to claim 2, wherein the anion is chloride.

26. The process according to claim 3, wherein the cation is sodium.

27. The process according to claim 6, wherein the salt is made of a cation selected from the group consisting of sodium, potassium and ammonium.

* * * * *